United States Patent [19]

Fauteux et al.

[11] Patent Number: 5,433,876
[45] Date of Patent: Jul. 18, 1995

[54] ION-CONDUCTIVE POLYMER AND ELECTROLYTE ADDITIVES

[75] Inventors: Denis G. Fauteux, Acton; Arthur A. Massucco, Natick; John R. Powell, Burlington; Martin F. van Buren, Chelmsford, all of Mass.

[73] Assignee: Arthur D. Little, Inc., Cambridge, Mass.

[21] Appl. No.: 76,005

[22] Filed: Jun. 9, 1993

Related U.S. Application Data

[63] Continuation-in-part of Ser. No. 996,101, Dec. 23, 1992.

[51] Int. Cl.$^6$ .................... H01M 6/18; C08F 18/00; C08G 2/00
[52] U.S. Cl. ................... 252/62.2; 429/191; 429/192; 527/300; 527/301; 527/302; 527/312; 527/313; 527/314; 527/315
[58] Field of Search ............... 252/62.2; 429/191, 192; 527/300, 301, 302, 312, 313, 314, 315

[56] References Cited

U.S. PATENT DOCUMENTS

| | | |
|---|---|---|
| 4,303,748 | 12/1981 | Armand et al. . |
| 4,357,401 | 11/1982 | Andre et al. . |
| 4,471,037 | 9/1984 | Bannister . |
| 4,556,614 | 12/1985 | le Mehaute et al. . |
| 4,578,326 | 3/1986 | Armand et al. . |
| 4,818,643 | 4/1989 | Cook et al. . |
| 4,818,644 | 4/1989 | Armand . |
| 4,830,939 | 5/1989 | Lee et al. . |
| 4,840,856 | 6/1989 | Nakacho et al. . |
| 4,844,995 | 7/1989 | Noda et al. . |
| 4,888,257 | 12/1989 | Narang . |
| 4,925,751 | 5/1990 | Shackle et al. . |
| 5,041,346 | 8/1991 | Giles . |
| 5,063,124 | 11/1991 | Gauthier et al. . |
| 5,077,073 | 12/1991 | Ennis et al. . |
| 5,098,589 | 3/1992 | Motogami et al. ............. 252/62.2 |
| 5,102,751 | 4/1992 | Narang et al. . |

FOREIGN PATENT DOCUMENTS

| | | |
|---|---|---|
| 0394496A1 | 10/1990 | European Pat. Off. . |
| 425255 | 5/1991 | European Pat. Off. . |
| 0504410A1 | 9/1992 | European Pat. Off. . |
| 0507004A1 | 10/1992 | European Pat. Off. . |
| 3149705 | 6/1991 | Japan . |
| 3156803 | 7/1991 | Japan . |
| 2164047 | 3/1986 | United Kingdom . |
| WO93/16108 | 8/1993 | WIPO . |

*Primary Examiner*—Stephen Kalafut
*Assistant Examiner*—Alan D. Diamond
*Attorney, Agent, or Firm*—Choate, Hall & Stewart

[57] ABSTRACT

Compounds are provided for use in an electrolyte comprising repeating unit selected from the group consisting of cyclic and heterocyclic species having y carbon atoms and z heteroatoms, X, and where y is 4, 5 or 6 and z is 0, 1 or 2. The heteroatom is selected from the group consisting of O, S and N. The repeating unit is further substituted by four to six pendant groups having the formula, $(CHR_1)_mO(CHR_1CHR_1O)_nY$, where the majority of pendant groups comprises at least two O and further, in which m is 0 or 1, in which n is in the range of 0 to 25, in which each $R_1$ is the same or different and $R_1$ is selected from the group consisting of H, alkyl, allylic and alkenyl radicals having 1 to 18 carbon atoms and Y, and in which each Y is the same or different and Y is a functional group selected from the group consisting of polymerizable functionalities, plasticizing agents and ionic species. Electrolytes, plasticizers and macro-ions prepared from these compounds are described.

14 Claims, 1 Drawing Sheet

ION-CONDUCTIVE POLYMER AND ELECTROLYTE ADDITIVES

This application is a continuation-in-part application of co-pending U.S. Ser. No. 07/996,101 filed Dec. 23, 1992, also entitlted "Ion-Conductive Polymer and Electrolyte Additives".

BACKGROUND OF THE INVENTION

This invention relates to electrolyte solvent and/or electrolyte additives for electrolytic cells and electrochemical devices, such as batteries, capacitors, fuel cells and displays, prepared therefrom. It further relates to novel electrolyte compositions for electrolytic cells.

Success of an alkali metal-based electrochemical devices requires the use of aprotic solvent-based electrolytes. These electrolytes must be electrochemically stable towards both cathode and anode materials. In devices such as batteries, these electrolytes must be highly conductive in order to allow useful current to be drained during use.

Current liquid aprotic electrolytes are characterized by low ionic conductivity and poor electrochemical stability. The latter leads to decomposition of the electrolyte. Decomposition products then lead to the formation of highly resistive layers at the surface of the electrodes (high interfacial impedance), which further limits the current density and useful cycle life of the device. This represents a major obstacle to the development of an alkali metal-based electrochemical device technology.

In order to overcome the difficulties inherent in liquid electrolytes, solid polymer electrolyte (SPE) materials have been developed in which ion mobility is possible through coordination of an electrolyte ion with suitable sites on the polymeric chain. Prior art polymer electrolytes have used high molecular weight polyethers (PEO) as solvents. However, PEO is crystalline at ambient temperature (20° C.) with an adverse effect on the conductivity.

Gel-polymers, in which plasticizers, such as dimethoxyethane, propylene and ethylene carbonate and acetonitrile, are added to the polymer, have also been used as solvents. The lower molecular weight plasticizers are of lower viscosity and allow greater segmental motion in the polymer, thereby enhancing ion mobility in solution. Addition of plasticizer increases conductivity to a value approaching that of the plasticizer-alone conductivity and also decreases the temperature dependence of conductivity. However, most of the prior art plasticizers are unsuitable for use in alkali metal-based batteries because they have higher vapor pressures and/or are unstable with respect to alkali metals. In these respects, gel polymers are similar to aprotic liquid electrolyte systems.

Another problem which arises in current solid polymer electrolyte technology is anionic polarization in the electrolyte layer. The anions migrate during use, thereby forming a charge gradient in the electrolyte. The anions migrate only very slowly back to their original position resulting in prolonged polarization of the cell. Therefore, attempts have been made to prepare a single-ionic mobility solid polymer electrolyte in which only the cations are mobile, while the anions are fixed to the polymeric chain.

In U.S. Pat. No. 5,098,589 to Motogami et al., a solid polymer for use in an electrolyte is disclosed which is formed by cross-linking an organic compound derived from glycerol and having an average molecular weight of 1,000 to 20,000. The compound contains block copolymer alkoxy pendant groups with substituent alkoxy groups extending therefrom. The pendant groups terminate in an active hydrogen or a polymerizable functional group. Cross-linking or polymerization of the organic compound takes place either at the polymerizable functional group or at the active hydrogen site. Conductivity at room temperature was in the range of $2.9$–$3.8 \times 10^{-5}$ S/cm.

In U.S. Pat. No. 4,357,401 to Andre et al., a solid polymer electrolyte, a so-called "linear star polymer", based on diaminoethylene and containing block copolymer ethylene and propylene oxide pendant groups is disclosed. Cross-linking occurs through active hydrogen sites at the pendant termini to provide a polymeric material with a conductivity in the range of $1$–$40 \times 10^{-5}$ S/cm at 100° C.

U.S. Pat. No. 5,059,443, discloses alkoxylated glucose derivatives containing fatty acid functional end groups for use as a fat substitute. The electrolytic properties of these derivatives were not investigated.

Thus far, none of the existing polymer electrolyte materials provide high ionic conductivity, high electrochemical stability and good mechanical properties at useful temperatures (preferably ambient). In addition, prior art liquid and solid polymer electrolytes do not allow for the promotion of the mobility of the ionic species of interest. This lack of control over these critical parameters greatly limits the performance, safety and cycle life of the existing alkali metal electrochemical device technologies. The present invention overcomes the above-stated limitations of the prior art.

It is the object of the present invention therefore, to provide a solid polymer electrolyte with improved conductivity and electrochemical stability and, optionally, with self-plasticizing capability.

It is a further object of the present invention to provide improved plasticizers with low vapor pressure, high conductivity and electrochemical stability and compatibility with a variety of electrolytes and cathode and anode materials.

It is yet a further object of the invention to provide an electrolytic species having high cationic mobility (high cationic transport number) and low anionic mobility.

SUMMARY OF THE INVENTION

In one aspect of the invention, a compound is provided for use in an electrolyte. The compound includes a cyclic or polycyclic backbone consisting of 1 to 10 repeating unit, $C_yX_z$, where the repeating unit is selected from the group consisting of cyclic and heterocyclic species having y carbon atoms and z heteroatoms, X, and where y is 4,5 or 6 and z is 0, 1 or 2. The heteroatom is selected from the group consisting of O, S and N.

The repeating unit, $C_yX_z$, is further substituted by four to six pendant groups having the formula, $(CHR_1)_mO(CHR_1CHR_1O)_nY$, where the majority of pendant groups comprises at least two O and further, in which m is 0 or 1, in which n is in the range of 0 to 25, in which each $R_1$ is the same or different and $R_1$ is selected from the group consisting of H, alkyl, allylic and alkenyl radicals having 1 to 18 carbon atoms and Y, and in which each Y is the same or different and Y is a functional group selected from the group consisting of polymerizable functionalities, plasticizing agents and ionic species. The ionic species contains a cation from the alkali metal or alkaline earth elements. Unless otherwise stated, the number of each n is an average.

Furthermore, to obtain superior electrolytic properties, the morphology of the above and subsequently disclosed compounds should be characterized by a compact backbone and extended pendant groups that is, a "star compound". By "star compound", as that term is used herein, it is meant that the compound possesses a dense core for supporting pendant groups. The core may be cyclic or linear or a combination of cyclic and linear repeating units. The pendant groups extend outward and away from the core, so as to impart to the compound a star-like appearance. The morphology of the compound plays an important role in its performance as an electrolyte constituent. The extended branched arrangement of the pendant groups increases chain mobility and thereby reduces the tendency of the compound to crystallize (decreases $T_g$).

By "plasticizing agent", as that term is used herein, it is meant any non-reactive, electrochemically stable functional group that does not contribute to the crystallinity of the compound.

By "alkali metal" as that term is used herein, it is meant the Group Ia metals of the Periodic Table of the Elements, including lithium, sodium, potassium, rubidium and cesium. By "alkaline earth metal", as that term is used herein, it is meant the Group IIa metals of the Periodic Table of the Elements, including beryllium, magnesium, calcium, strontium and barium.

The compound is used in an electrolyte with an electrolytic salt. The cation of the electrolytic salt is solvated by the oxygen of the pendant groups. It has been observed that at least two oxygen per pendant group are required for most of the pendant groups to effect the solubilization of the cation.

In another aspect of the invention, a functionalized alkoxylated carbohydrate, such as monosaccharides and oligosaccharides, is provided for use in an electrolyte. The saccharide moiety is selected from the group consisting of pentoses and hexoses and typically has one to five hydroxyl groups. The hydroxyl groups are substituted with a total of between 4 and 150, and preferably a total of between 4 and 60, alkoxy groups attached through ether linkages. The alkoxy groups terminate in a hydroxyl group. Each terminal hydroxyl group of the carbohydrate is then functionalized with a functional group, Y, selected from the group consisting of polymerizable functionalities, plasticizing agents and ionic species.

By "carbohydrate", as that term is used herein, it is meant a compound comprised of sugars, sugar alcohols or dehydrated sugar alcohols. "Sugar alcohol" is used in the conventional sense as the reduction product of sugars, wherein the aldehyde or ketone group is reduced to an alcohol.

By "oligosaccharide", as that term is used herein, it is meant polysaccharides that yield from two to ten monosaccharide units upon hydrolysis.

In another aspect of the invention, a solid polymer electrolyte is provided which contains a solvated cation and a polymer constituted from a compound comprising a linear backbone having 1 to 20 repeating units, $C_iX_j$, where the repeating unit is selected from the group consisting of saturated and unsaturated alkyl and alkenyl species containing i carbon atoms and j heteroatoms, X, where i is in the range of 1 to 6 and j is in the range of 0 to 3. The heteroatom, X, is selected from the group consisting of O, S, and N.

The repeating unit, $C_iX_j$, further is substituted by one to six pendant groups having the formula, $(CHR_1)_mQ(CHR_1CHR_1Q)_nY$. The pendant group is selected such that a majority of the pendant groups contains at least two Q and further, in which m is 0 or 1,
in which n is in the range of 0 to 25,
in which Q is a Group Ia or Group IIa cation-solvating species selected from the group consisting of O, S and $NR_1$,
in which each $R_1$ is the same or different and $R_1$ is selected from the group consisting of H, alkyl, allylic and alkenyl radicals having 1 to 18 carbon atoms and Y, and
in which each Y is the same or different and Y is a functional group selected from the group consisting of polymerizable functionalities, plasticizing agents and ionic species, wherein at least one Y is a polymerizable functionality and at least one Y is a functionality other than a polymerizable functionality. Unless otherwise stated, the number of each n is an average.

The cation may be a monovalent or divalent cation selected from the Group Ia and Group IIa elements. The cation should be capable of solvation by "Q" of the pendant group, which is oxygen, nitrogen or sulfur. As stated above, most pendant groups should have at least two Q to effect solvation of the cation.

In another aspect of the invention, a solid polymer electrolyte is provided which contains a solvated cation and a polymer constituted from a compound comprising a backbone having 1 to 10 repeating units, $C_aX_b$, where the repeating unit is selected from the group consisting of saturated and unsaturated cyclic and heterocyclic species and saturated and unsaturated alkyl and alkenyl species containing a carbon atoms and b heteroatoms, X, where a is in the range of 1 to 8 and b is in the range of 0 to 10. The heteroatom is selected from the group consisting of O, S, and N. At least one repeating unit comprises a cyclic species.

The repeating unit, $C_aX_b$, further is substituted by one to six pendant groups having the formula, $(CHR_1)_mQ(CHR_1CHR_1Q)_nY$. The pendant group is selected such that a majority of the pendant groups comprises at least two Q and further, in which m is 0 or 1,
in which n is in the range of 0 to 25,
in which Q is a Group Ia or Group IIa cation-solvating species selected from the group consisting of O, S and $NR_1$,
in which each $R_1$ is the same or different and $R_1$ is selected from the group consisting of H, alkyl, allylic and alkenyl radicals having 1 to 18 carbon atoms and Y, and
in which each Y is the same or different and Y is a functional group selected from the group consisting of polymerizable functionalities, plasticizing agents and ionic species, wherein at least one Y is a polymerizable functionality. Unless otherwise stated, the number of each n is an average. The cation may be a monovalent or divalent cation selected from the Group Ia and Group IIa elements.

The selection of a particular functional group for Y imparts specific desirable properties to an electrolyte comprising the above compounds. As used herein, when the compound contains polymerizable functional groups, the compound is referred to as a "monomer". When the compound contains no polymerizable functionalities, the compound is referred to as an "electrolyte additive". Electrolyte additives include plasticizers and electrolyte salts.

The pendant group may be functionalized with a polymerizable functionality to provide a monomer capable of cross-linking or polymerizing to form a high molecular weight polymer of high ionic conductivity. At least one Y of the compound must be a polymerizable functionality to form a solid polymer electrolyte. A polymerizable functionality may be an epoxide, an isocyanate, an acrylate or an alkenyl group. The polymerizable functionality is not intended to include an active hydrogen for enhanced safety in alkali metal-based electrochemical devices.

The pendant group may be functionalized with a plasticizing agent. If a monomer additionally contains a plasticizing agent, it is designated a "selfplasticizing" monomer. By "self-plasticizing", as that term is used herein, it is meant that the polymer contains pendant groups which impart to the polymer desirable properties, such as improved mechanical properties and reduced crystallinity at room temperature, through increased segmental motion. If a compound contains only plasticizing agents as Y groups, it functions as a plasticizer. A plasticizer of the present invention is a good ionic solvent, typically a liquid, that is non-volatile and non-reactive. A plasticizing agent may be a trialklysilyl, an alkyl, a phosphate ester, phosphinate ester or a saturated ester group.

The pendant group may be functionalized with an ionic species. An ionic species provides cation of the Group Ia or IIa elements for use as an electrolytic species. A compound containing at least one and ranging up to only ionic species results in a macro-ion. Because of its large size, the anion is effectively anchored in place, so that primarily the cation is mobile. The ionic species may be an alkali metal or alkaline earth salt of an alkoxide or an alkyl or haloalkyl carboxylate or sulfonate.

The present invention provides the capability of tailoring the individual compounds to thereby impart unique properties to the electrolyte. In particular, the compounds of the present invention may contain only one type of functional group or any combination of functional groups. For example, monomers having both polymerizable and plasticizing functionalities can be polymerized with compounds having both polymerizable and ionic functionalities, thereby providing a polymer having all three functionalities. The overall composition of the polymer can be easily adjusted by changing the relative proportions of the variously functionalized monomers.

Mixtures of monomer and electrolyte additives can be used to further tailor the electrolyte composition. Upon polymerization, the monomers participate in the polymerization reaction to form a polymer, while electrolyte additives without polymerizable functionalities do not. The result is an intimately mixed composite material of polymer and electrolyte additive. The electrolyte additive can be a plasticizer to help improve the conductivity and mechanical properties of the electrolyte. The electrolyte additive can be a macro-ion to provide a soluble cation and a macroanion for the electrolyte.

Compounds of the present invention can also be used as electrolyte additives, such as plasticizers and macroions, in conventional electrolyte systems, such as primary and rechargeable liquid electrolyte lithium batteries. They also can be used in the preparation of composite electrodes.

The above-described electrolytes can be used with negative and positive electrodes in an electrochemical device, such as a battery, capacitor, fuel cell or display.

DETAILED DESCRIPTION OF THE INVENTION

Figure 1:
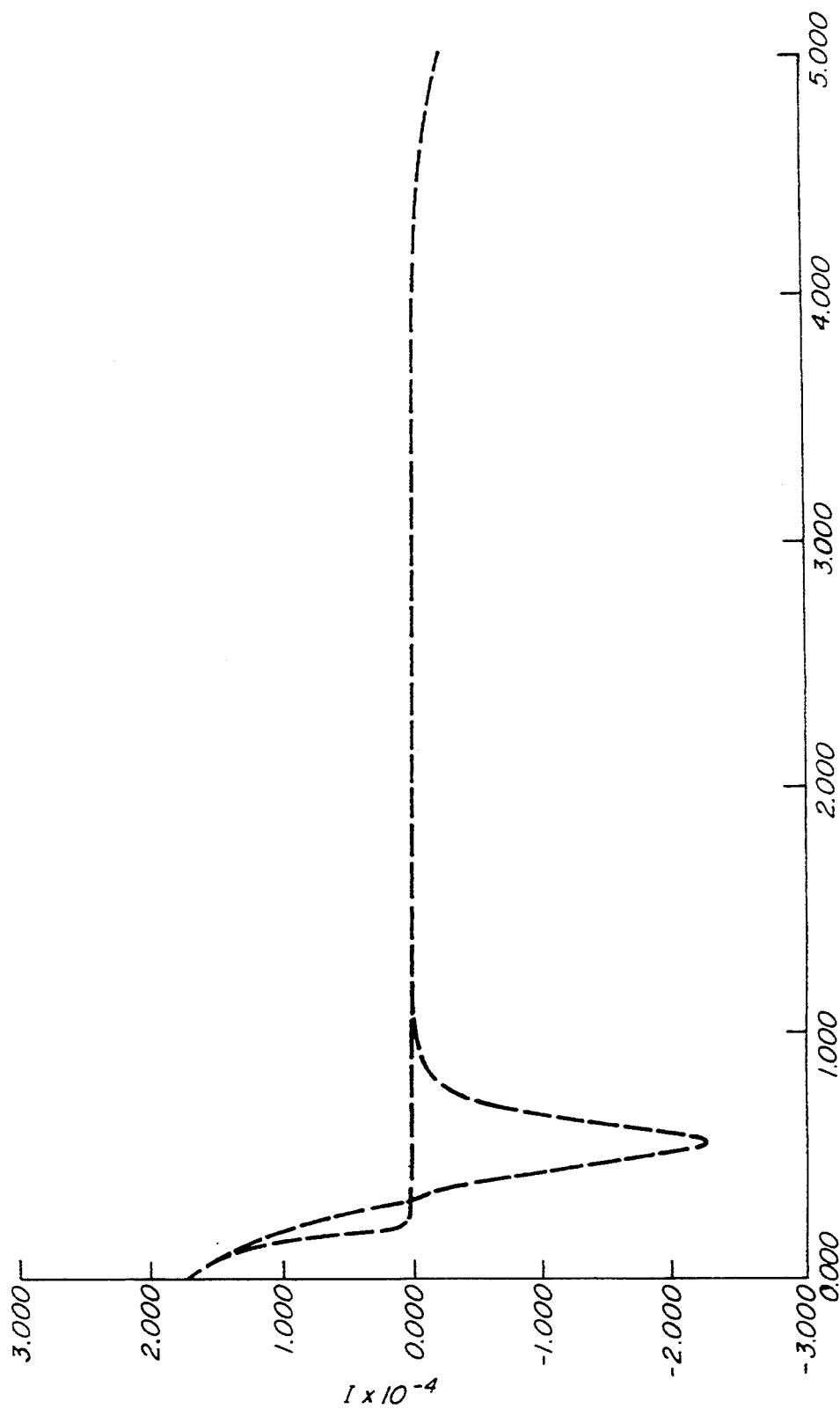
FIG. 1 is a cyclic voltammogram of an electrochemical cell using an electrolyte of the invention over a range of 0 to 5 V.

The present invention has recognized that certain classes of materials, as described herein, exhibit excellent ionic conductivity and thermal and electrochemical stability when used in an electrolyte.

The compounds of the present invention have the following features in common: a compact backbone, extended pendant groups containing cation-solvating species and functionalizing groups which impart desirable properties to the electrolyte. The compounds of the present invention are highly versatile in that the nature and relative proportions of the functionalizing groups can be readily altered. These compounds are useful as monomers in preparing solid polymer electrolytes and as electrolyte additives, such as plasticizers and macro-ions.

The compact backbone of the compounds used in the invention may have a repeating structure of the general formula, $C_iX_j$, selected from the group consisting of linear saturated and unsaturated alkyl and alkenyl species containing i carbon atoms and j heteroatoms, where i is in the range of 1 to 6, where j is in the range of 0 to 3. The heteroatom, X, is selected from the group consisting of O, S, and N. In particular, the repeating structure may be alkylene imine, diaminoalkyl, alkoxy groups, such as ethoxy or propoxy and the like, or their thio-derivatives.

Alternately, the compact backbone may have a repeating structure of the general formula, $C_aX_b$, selected from the group consisting of saturated and unsaturated cyclic and heterocyclic species and linear alkyl and alkenyl species containing a carbon atoms and b heteroatoms, where a is in the range of 1 to 8 and b is in the range of 0 to 4. The heteroatom is selected from the group consisting of O, S, and N. At least one repeating structure comprises a cyclic or heterocyclic species. In particular, the repeating structure may be cyclic alkyl groups, such as cyclohexyl and cyclopentyl and the like, cyclic ethers and their thio-derivatives, such as furanyl, tetrahydrofuranyl, thiophenyl, pyranyl, tetrahydropyranyl, dioxanyl, trioxanyl and the like, and cyclic amino groups such as pyrolidinyl and piperidinyl and the like. The repeating structure may also include alkylene imine, diaminoalkyl, and alkoxyl groups, such as ethoxy or propoxy and the like, and their thio-derivatives.

A particularly preferred compound has a repeating structure of the general formula, $C_yX_z$, selected from the group consisting of cyclic and heterocyclic species consisting of y carbon atoms and z heteroatoms, X, where y is 4, 5 or 6 and z is 0, 1 or 2. The heteroatom is selected from the group consisting of O, S and N. The repeating structure, $C_xX_y$, may be a group such as cyclic alkyl groups, such as cyclohexyl and cyclopentyl and the like, cyclic ethers and their thio-derivatives, such as furanyl, tetrahydrofuranyl, thiophenyl, pyranyl, tetrahydropyranyl, dioxanyl, trioxanyl and the like, and cyclic amino groups such as pyrolidinyl and piperidinyl and the like.

Certain classes of preferred compounds for use in the electrolyte of the present invention may be conveniently prepared from carbohydrates in their cyclic form. The carbohydrate possesses a plurality of pendant hydroxyl groups that can be readily converted into the extended pendant chains of the present invention. A functionalized alkoxylated carbohydrate for use in an electrolyte includes monosaccharide moieties selected from the group consisting of pentoses and hexoses and having one to five hydroxyl groups, wherein a total of between 4 and 150 and preferably between 4 and 60 alkoxy groups are attached through ether linkages to the hydroxyl group of each monosaccharide moiety and wherein each alkoxide-substituted hydroxyl group of the monosaccharide moiety is functionalized with a functional group, Y, selected from the group consisting of polymerizable functionalities, plasticizing agents and ionic species. Oligosaccharides comprising monosaccharide moieties described above are also contemplated.

Suitable carbohydrates include monosaccharides and oligosaccharides which provide a variety of templates for derivatization. Five- or six-membered cyclic monosaccharaides, such as glucose, fructose, sorbose, mannose, ribose, xylose and the like; disaccharides, such as sucrose, maltose, lactose and the like; and trisaccharides, such as raffinose, are particularly preferred templates.

The pendant groups of the compounds of the invention contain elements, such as oxygen, sulfur or nitrogen, which are capable of solvating cations of the Group Ia and IIa elements. The pendant group can be an alkoxy group, such as ethoxy, propoxy and the like or its thio derivatives; or an alkylene imine. The pendant group provides a branching side chain which can solvate the electrolyte cation or help form a network polymer upon polymerization. The chain length of the extended pendant group also contributes to the formation of a macroanion by helping to anchor the macroanion in the electrolyte.

Among the polymerizable functionalities, there are included alkenyl groups, isocyanates, epoxides and unsaturated carboxyl groups. Such polymerizable functionalities, include but are in no way limited to, alkenyl groups such as vinyl and allyl; unsaturated carboxyl compounds such as acrylate, methacrylate, cinnamate, fumarate, maleate and the like; isocyanates such as methylisocyanate and the like; and halosilyl groups, such as dimethyl chlorosilyl and the like. In particular, the polymerizable functionality can include

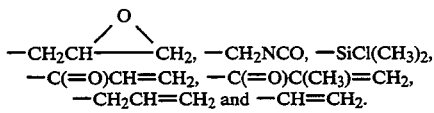

$-CH_2CH(O)CH_2$, $-CH_2NCO$, $-SiCl(CH_3)_2$,
$-C(=O)CH=CH_2$, $-C(=O)C(CH_3)=CH_2$,
$-CH_2CH=CH_2$ and $-CH=CH_2$.

Unless otherwise stated, cross-linking functionalities can be used as polymerizable functionalities, in that, they both perform the function of increasing the molecular weight of the network polymer. Polymerization can be carried out using standard techniques, including photoinitiation and thermal and chemical initiation.

Among the plasticizing agents, there are included, but in no way are limited to, trialklysilyl, alkyl, nitrilic, phosphate ester, phosphinate ester and saturated ester groups. In particular, these include, trimethyl- or triethylsilyl; alkyl groups such as methyl, ethyl and the like; phosphate ester groups such as diethyl phosphatyl and diphenyl phosphatyl; diphenyl phosphinatyl; alkylnitrile and saturated alkyl esters such as acetate, isobutyrate and the like. In particular, the plasticizing agent includes $-Si(CH_3)_3$, $-CH_3$ and $-C(=O)CH_3$. In general, plasticizing agents can include non-reactive, electrochemically stable functional groups that do not contribute to the crystallinity of the compound.

In an important aspect of the invention, an electrolyte is prepared using the compounds of the invention and a soluble cation. The cation is introduced as an ionic functional group on the pendant group of the compound. In this instance, the compound functions as a macro-ion. Among the ionic functional groups suitable for use in the macro-ion of the present invention, there are included, but are in no way limited to, alkali metal and alkaline earth salts of alkoxides, alkyl carboxylates and sulfonates and haloalkyl carboxylates and sulfonates.

It may also be desirable to introduce some or all of the soluble cation as a soluble electrolyte salt of the prior art. Among the soluble electrolyte salts suitable for use in the electrolyte of the present invention, there are included, but in no way limited to, inorganic ion salts containing a cation selected from the Group of Ia and IIa elements associated with anions such as $ClO_4^-$, $SCN^-$, $BF_4^-$, $AsF_6^-$, $CF_3SO_3^-$(triflate),$Br^-$, $I^-$, $PF_6^-$, $(CF_3SO_2)_2N^-$ (bis(trifluoromethanesulfonyl)imide or TFSI), $(CF_3SO_2)_3C^-$ (tris(trifluoromethanesulfonyl)methide or TFSM), $CF_3CO_2^-$ and the like. In particular, lithium ion is the preferred cation.

By incorporating plasticizing agent functional groups onto pendant chains that also include polymerizable functional groups, followed by polymerization, the polymer becomes self-plasticizing. This is particularly desirable because the polymer, while exhibiting the properties of a solid polymer electrolyte film retains an amorphous, non-crystalline morphology with a high degree of segmental mobility of the pendant chains at room temperature. As a consequence, the need for a liquid plasticizer of the prior art can be eliminated.

Plasticizers and soluble alkaline metal macro-ions of the present invention can be incorporated into conventional electrolyte systems. Such electrolytes include, but are in no way limited to, ethylene carbonate, propylene carbonate, dimethoxyethane and sulfolane. When the plasticizers and soluble macro-ions of the present invention are incorporated into conventional electrolyte systems, the resultant electrolyte exhibits improved electrochemical properties and reduced anion mobility, respectively.

A composite electrode can be prepared containing an electrochemically active compound, carbon as an electronic conductor and monomers of the present invention. Upon polymerization, a solid composite material is obtained containing electrode active materials and an ionically conductive solid polymer of the present invention.

Preferred Embodiments of the Invention

Other characteristics and advantages of the invention are illustrated, but in no ways limited to, the following examples.

The starting materials for the following examples is an ethoxylated methyl glucoside. CFTA-adopted names for such compounds are methyl gluceth-10 ["MG-10"] and methyl gluceth-20 ["MG-20"], respectively. Propoxylated derivatives are designated PPG methyl gluceth-10 ["PPG-10"] and PPG methyl gluceth-20 ["PPG-20"], respectively. The material is commercially available as Glucam ® (Amerchol Corp., Talmadge Rd., Edison, N.J.). Glucam ® is offered as derivatives of both ethylene oxide (Glucam ®-E) and propylene oxide (Glucam ®-P) and having an average of 10 or 20 ethoxy or propoxy groups per molecule.

Other alkoxylated glucosides with various molecular weights could also be used as a starting material. The desired alkoxylated starting materials can be prepared by reacting I mole of methyl glucoside with the desired moles of an alkylene oxide, for example, ethylene oxide, to form an ethoxylated methyl glucoside, which has 4 primary hydroxyl groups available for reaction.

Other alkoxylated saccharides with various molecular weights could also be used as a starting material. The desired alkoxylated starting materials can be prepared by reacting I mole of saccharide with the desired moles of an alkylene oxide, for example, ethylene oxide, to form an ethoxylated saccharide, the number of primary hydroxyl groups available for reaction is dependent upon the initial degree of hydroxyl group substitution on the backbone.

Other backbones with different structures could also be used as a starting material. The desired alkoxylated starting materials can be prepared by reacting I mole of a selected backbone containing pendant hydroxyl groups with the desired moles of an alkylene oxide to form an alkoxylated starting material, the number of primary hydroxyl groups available for reaction dependent upon the initial degree of hydroxyl groups substitution by the backbone.

Examples 1–4 present a method of preparing plasticizer-functionalized compounds.

Example 1

An acetylethoxylated methyl glucoside according to the present invention is prepared as follows. A cyclohexane solution of MG-20 (50.0 g, 0.048 mole) and sodium acetate (6.49 g, 0.0791 mole, Fisher Scientific) is heated to the cyclohexane refluxing temperature (80° C). Traces of water are removed from the system as the cyclohexane azeotrope and collected in the receiver. When refluxing removes no additional water, acetic anhydride (19.94 g, 0.196 mole, Fisher Scientific) is slowly added to the stirred and refluxing mixture in the flask over a 1 hr. period, and the flask then cooled to room temperature. About 150 ml distilled water is added to the flask's contents and then stirred. Concentrated NaOH solution is added to raise the pH to above 7.0. The cyclohexane organic phase is separated from the aqueous phase. The aqueous phase is then extracted twice with two 150 ml portions of chloroform. The product is isolated by concentrating the dried chloroform extract in a rotary flash evaporator at about 55° C. until no additional solvent is removed. Yield of acetylethoxylated methyl glucoside (MG-20-ACETYL$_4$) is 46.45 g (80% theoretical). The nomenclature indicates functionalization with four acetyl groups per glucoside backbone.

The product is a clear, pale yellow, viscous fluid with no odor. Confirmation of the product's identity is made by infrared spectroscopy.

Example 2

A trimethylsilylethoxylated methyl glucoside according to the present invention is prepared as follows. MG-20 (1003 g, 0.981 mole), triethylamine (479 g, 4.73 mole, Aldrich Chemical Co.), and tetrahydrofuran (4000 ml, THF) are stirred briefly in a round bottom flask to form a clear, colorless solution, and a slightly positive pressure of argon gas maintained in the reaction flask. Trimethylchlorosilane (513.6 g, 4.73 mole, Aldrich Chemical Co.) is diluted with THF (780 ml). Onethird (500 ml) of the trimethylchlorosilane/THF solution is slowly added to the reaction flask's contents while stirring the reaction mixture. A large volume of white precipitate (triethylamine hydrochloride) forms in the reaction mixture almost immediately. The remaining two-thirds of the trimethylchlorosilane/THF solution is then slowly added to the reaction flask accompanied by the formation of additional precipitate. The complete addition is made over a period of 3 hr. 15 min. During the addition the temperature of the flask's contents rises from room temperature to about 34° C. Stirring is continued for an additional 2 hr, while the flask cools to room temperature. The triethylamine hydrochloride precipitate is removed by filtration. The crude product solution is concentrated in a rotary flash evaporator at about 35° C. and is then diluted with about 2000 ml hexanes. After stirring, the solution is filtered to remove all traces of triethylamine hydrochloride. The product is isolated by concentrating the hexane solution in a rotary flash evaporator at about 45° C. Yield of trimethylsilylethoxylated methyl glucoside (MG-20-TMS$_4$) is 1246 g (96.6% theoretical). The nomenclature indicates four trimethylsilyl groups per glucoside backbone.

The product is a clear, pale yellow, oily fluid with no odor. Confirmation of the product's identity is made by infrared spectroscopy.

Example 3

A tetrakis(diethylphosphatyl) ethoxylated methyl glucoside according to the present invention is prepared as follows.

MG-20 (50.0 g, 0.048 mole) in dry tetrahydrofuran (250 ml) and triethylamine (19.8 g, 0.196 mole, Aldrich Chemical Co.) is charged to a 1000 ml 3-neck round bottom flask equipped with an argon gas purge, a refluxing condenser, a thermometer, an addition funnel, heating mantle, and magnetic stirrer, and the resulting solution is stirred. Diethyl chlorophosphate (33.8 g, 0.196 mole, Aldrich Chemical Co.) in THF (50 ml) is slowly added to the stirred flask over a 1 h. period. A large volume of white precipitate (triethylamine hydrochloride) forms in the reaction mixture almost immediately. During the addition, the temperature of the flask's contents rises from room temperature to about 34° C. The flask's contents are heated to the reflux temperature of THF for 4 hs., and then cooled to room temperature. The flask's contents stored under argon at 5° C. overnight.

The triethylamine hydrochloride precipitate is removed from the THF/product solution by suction filtration. The crude product solution is concentrated in a rotary flash evaporator at about 35° C. until no additional THF is removed and is then diluted with about 500 ml hexanes/ether. After stirring for about 2 h. the solution is filtered to remove all traces of triethylamine hydrochloride, dried over anhydrous magnesium sulfate and filtered through a basic alumina column. The product is isolated by concentrating the solution in a rotary flash evaporator at about 45° C. until no additional solvent is removed. The product is a transparent orange oil. Yield of tetrakis(diethylphosphatyl) exthoxylated methyl glucoside [MG-20-(PO$_3$Et$_2$)$_4$] is 83 g (58% theoretical).

Example 4

A tetrakis (diphenylphosphinatyl) ethoxylated methyl glucoside according to the present invention is prepared as follows.

Diphenylphosphinic chloride (37.1 g., 0.157 mole, Aldrich Chemical Co.) in dry tetrahydrofuran (100 ml) and triethylamine (18.2 g, 0.179 mole, Aldrich Chemical Co.) is charged to a 500 ml 3-neck round bottom flask equipped with an argon gas purge, a refluxing condenser, an addition funnel, heating mantle, and magnetic stirrer, and the resulting solution stirred. MG-10 (19.3 g., 0.0317 mole) in THF (100 ml), is slowly added to the stirred flask over a 30 min. period. A large volume of white precipitate (triethylamine hydrochloride) forms in the reaction mixture almost immediately. During the addition, the temperature of the flask's contents rises from room temperature to about 34° C., and the mixture increases in viscosity. More THF (100 ml) is added to the flask to reduce the mixture's viscosity. The flask's contents are heated to the reflux temperature of THF for 5 hr. then cooled to room temperature. The flask's contents stored under argon at 5° C. overnight.

The triethylamine hydrochloride precipitate is removed from the THF/product solution by suction filtration. The crude product solution is concentrated in a rotary flash evaporator at about 35° C. until no additional THF is removed and then is diluted with about 300 ml toluene and 40 ml methylene chloride. The solution is dried over anhydrous magnesium sulfate and filtered. The product is isolated by concentrating the solution in a rotary flash evaporator at about 45° C. until no additional solvent is removed. Finally, the product is heated in a vacuum chamber at 105° C. for 8 h. to remove residual toluene. The product is a very high viscosity transparent amber oil. Yield of tetrakis (diphenylphoshinatyl) ethoxylated methyl glucoside [MG-10(POPh$_2$)$_4$] is 44.7 g (100% theoretical).

Example 5

This example presents a method of preparing an ionic sulfonate derivative.

A sodium sulfopropylethoxylated methyl glucoside salt according to the present invention is prepared as follows. A solution of MG-20 (49.4 g, 0.048 mole), 1,3-propane sultone (27.5 g, 0.225 mole, Aldrich Chemical Co.) and N-methyl pyrolidone (NMP) (50 ml) is prepared. Sodium hydride (5.40 g, 0.225 mole) in 100 ml NMP is charged to a round bottom flask and the MG-20/1,3-propane sultone/NMP solution is introduced through dropwise addition. During the addition, vigorous effervescence of hydrogen gas occurs and the temperature of the flask's contents rises from room temperature to about 38° C. After addition is complete, the reactants are gently warmed with continuous stirring to about 55° to 70° C. for several hours and then allowed to cool overnight to room temperature. Gentle heating during the day followed by cooling overnight is repeated for the next 4 days. The reaction mixture is then slowly poured into a rapidly stirred solution of methyl t-butyl ether (MTBE) (300 ml) and methanol (15 ml). The product sulfonate precipitates as a light tan powder. The precipitated product is extracted in a Soxhlet thimble with hot (55° C.) MTBE for about 45 min. The product is then held at 60° C. and 30 inches Hg vacuum until constant weight is obtained (24 hr). Yield of sodium sulfopropylethoxylated methyl glucoside (MG-20-Na) is 31.0 g (40.2% theoretical). There are four sodium sulfonate groups per glucoside backbone.

The product is a tan powder with no odor. It is extremely hygroscopic and will spontaneously form an aqueous solution on exposure to atmosphere. It is insoluble in most organic solvents, slightly soluble in methanol, soluble in NMP, and readily soluble in water. Confirmation of the product's identity is made by infrared spectroscopy and thin layer chromatography.

The sodium salt is converted into a lithium salt using conventional ion exchange methods.

Example 6

This example presents a method of preparing and polymerizing a polymerizable derivative. An acryloylethoxylated methyl glucoside according to the present invention is prepared as follows.

MG-20 (50.0 g, 0.048 mole) is diluted in dry methylene chloride (150 ml). This solution is stirred with anhydrous sodium carbonate (30 g, Fisher Scientific). Acryloyl chloride (16.1 g, 0.205 mole, Aldrich Chemical Co.) in methylene chloride (25 ml) is added dropwise to the solution over a 1 hr period and with a slight exothermic warming of the flask's contents. Stirring is continued overnight. The flask's contents are passed through a column of basic activated alumina (Aldrich Chemical Co.) to filter solids and remove acidic material from the product solution. The product is concentrated in a rotary flash evaporator at about 55° C. Yield of acryloylethoxylated methyl glucoside (MG-20-ACR$_4$) is 51 g (79% theoretical). There are four acryloyl groups per glucoside backbone. The product is a clear, yellow, oily fluid with a trace acrylic odor. Confirmation of the product's identity is made by infrared spectroscopy.

This product is converted to a hard, transparent, solid, polymer film by addition of a photoinitiator (0.1 wt % Darocure ® 1173, EM Industries, Inc.) to the acryloylethoxylated methyl glucoside, casting a 0.005 in film of the product/photoinitiator solution on glass with an adjustable film casting knife gapped at 0.010 in, and exposing the wet film to high intensity UV light (Fusion Systems H bulb) for about 0.2 sec.

Example 7

This example presents a method of preparing and polymerizing doubly-functionalized derivative having polymerizable and plasticizing groups. An acryloylethoxylated trimethylsilylethoxylated methyl glucoside with an average of about two polymerizable groups per glucoside according to the present invention is prepared as follows.

A solution is prepared of MG-20 (250.0 g, 0.245 mole), triethylamine (204.5 ml, Aldrich Chemical Co.), hydroquinone (0.050 g, Anachemia) and dry THF (1500 ml). Acryloyl chloride (38.4 g, 0.489 mole, Aldrich Chemical Co.) in THF (150 ml) is added dropwise to the stirred solution over 1.5 hr. A large volume of white precipitate (triethylamine hydrochloride) forms in the reaction mixture almost immediately. Trimethylchlorosilane (106.2 g, 0.98 mole, Aldrich Chemical Co.) in THF (250 ml) is added dropwise over 3.3 h to the stirring solution accompanied by the formation of additional precipitate. Stirring is continued for an additional 1.5 hr, while the flask cools to room temperature. The triethylamine hydrochloride precipitate is removed by filtration. The crude product solution is concentrated in a rotary flash evaporator at about 35° C. Some residual triethylamine hydrochloride precipitate forms when the product is concentrated. Crude product is then diluted with hexanes (750 ml)/ether (500 ml) and stored overnight at 10° C. The product solution is filtered to remove all traces of triethylamine hydrochloride. The product is isolated by concentrating the hexane/ether solution in a rotary flash evaporator at about 30° C. Yield of acryloylethoxylated trimethylsilylethoxylated methyl glucoside (MG-20-ACR$_2$,TMS$_2$) is 295 g (96% theoretical).

The product is a clear, yellow, oily fluid with a trace acrylic odor. Confirmation of the product's identity is made by infrared spectroscopy and thin layer chromatograph.

This product is converted to a transparent, solid, polymer film by addition of a photoinitiator (0.1 wt % Darocure® 1173, EM Industries, Inc.) to the acryloylethoxylated trimethylsilylethoxylated methyl glucoside, casting a 0.005 in film of the product/photoinitiator solution on glass with an adjustable film casting knife gapped at 0.010 in, and exposing the wet film to high intensity UV light (Fusion Systems H bulb) for about 0.2 sec.

Example 8

A acryloylethoxylated tris (diphenylphosphatyl) ethoxylated methyl glucoside with an average of about one polymerizable group per glucoside according to the present invention is prepared and polymerized as follows.

MG-10 (250.0 g, 0.245 mole), triethylamine (204.5 ml, Aldrich Chemical Co.), hydroquinone (0.050 g, Anachemia) and dry tetrahydrofuran (1500 ml)(THF) are charged to a round bottom flask equipped with a refluxing condenser capped with a calcium sulfate drying tube, a thermometer, an addition funnel, and a paddle type stirrer. Diphenyl chlorophosphate (197.5 g, 0.75 mole, Aldrich Chemical Co.) in THF (250 ml) is added dropwise to the stirred solution over a 1.5 h. period with a slight warming of the flask's contents to 30° C. A large volume of white precipitate (triethylamine hydrochloride) forms in the reaction mixture almost immediately. The contents of the flask are heated to the reflux temperature of THF for 3 h. and then cooled to room temperature.

Acryloyl chloride (23.0 g, 0.30 mole, Aldrich Chemical Co.) in THF (150 ml), is added dropwise over a period of 2 h to the stirred solution, accompanied by the formation of additional precipitate. During the addition the temperature of the stirred solution remains between 30° and 25° C. Stirring is continued for an additional 6 hr. at room temperature. The reactor is then stored overnight under dry air atmosphere.

The triethylamine hydrochloride precipitate is then removed from the THF/product solution by filtration. The crude product solution is concentrated in a rotary flash evaporator at about 35° C. until no additional THF is removed. Crude product is then diluted with methylene chloride, washed with several small volumes of 0.01N HCl, then dried over anhydrous magnesium sulfate and filtered through a basic alumina column. The product is isolated by concentrating the methylene chloride solution in a rotary flash evaporator at about 30° C. until no additional solvent is removed. Yield of acryloylethoxylated tris(diphenylphosphatyl) ethoxylated methyl glucoside [MG-10-ACR(PO$_3$Ph$_2$)$_3$] is 295 g. (69% theoretical).

The product is a clear, yellow, oily fluid with a trace acrylic odor. Confirmation of the product's identity is made by infrared spectroscopy and thin layer chromatography.

This product is converted to a transparent, solid, polymer film by addition of a photoinitiator (0.1 wt % Darocure® 1173. EM Industries, Inc.) to the acryloylethoxylated tris (diphenylphosphatyl) ethoxylated methyl glucoside, casting a 0.005" (0.0127 cm) film of the product/photoinitiator solution on glass with an adjustable film casting knife gapped at 0.010" (0.0254 cm), and exposing the wet film to high intensity UV light (Fusion Systems H bulb) for about 0.2 sec.

Example 9

Ionic conductivity of various alkoxylated compound-based electrolytes is determined.

Electrolyte solutions containing an ethoxylated glucoside or other alkoxylated compound and a lithium salt were prepared by dissolving 10% wt of lithium perchlorate in the compound of interest. The ionic conductivity of the electrolyte solutions were measured as at room temperature for various electrolyte compositions and are reported in Table 1. Note that the ionic conductivity of all these compounds even at room temperature is sufficient for most applications. Because of the hydroxyl end groups, nonfunctionalized alkoxylated compound-based electrolytes are not suitable for use with alkali metal electrodes, such as lithium. However, the measured ionic conductivity suggests that derivatives of these compounds could all be functionalized for use in the present invention.

TABLE 1

| Ionic Conductivity of unfunctionalized alkoxylated compound-based electrolytes. | |
|---|---|
| alkoxylated compound (% Li salt) | conductivity (S/cm) |
| PPG-10 (10% LiClO$_4$) | $1 \times 10^{-6}$ |
| PPG-20 (10% LiClO$_4$) | $8 \times 10^{-5}$ |
| MG-10 (10% LiClO$_4$) | $1.5 \times 10^{-5}$ |
| MG-20 (10% LiClO$_4$) | $8 \times 10^{-4}$ |
| Sorbeth-20 (10% LiClO$_4$) | $1.0 \times 10^{-4}$ |
| Sorbeth-40 (10% LiClO$_4$) | $1.3 \times 10^{-4}$ |
| Glycereth-26 (10% LiClO$_4$) | $1.1 \times 10^{-4}$ |
| Glycereth-7 (10% LiClO$_4$) | $1.3 \times 10^{-4}$ |
| Glycereth-35 (10% LiClO$_4$) | $8.7 \times 10^{-5}$ |

Example 10

Determination of the ionic conductivity of functionalized methyl glucoside-based electrolytes. An electrolyte solution containing trimethylsilylethoxylated methyl glucoside MG-20-TMS$_4$, as described in Example 2, and 10% wt of lithium tris(trifluoromethanesulfonyl)methide (LiTFSM) was prepared. An electrolyte solution containing acetylethoxylated methyl glucoside MG-20-ACETYL$_4$, as described in Example 1, and 10% wt of lithium bis(trifluoromethanesulfonyl)imide (LiTFSI) was prepared. Ionic conductivity were measured as a function of temperature and are reported in Table 2. The ionic conductivity of these functionalized ethoxylated methyl glucoside-based electrolytes is suitable for most applications even at room temperature. A threshold ionic conductivity of $10^{-5}$ S/cm is considered necessary for electrochemical devices. Advantageously, the functionalized derivatives, MG-20-TMS$_4$ and MG-20-ACETYL$_4$, can be used in lithium electrode environments.

TABLE 2

Ionic conductivity of functionalized ethoxylated methyl glucoside-based electrolytes.

| | Conductivity (S/cm) | |
|---|---|---|
| | T = 25° C. | T = 100° C. |
| MG-20-ACETYL, LiTFSI (10% wt) | $1.3 \times 10^{-4}$ | — |
| MG-20-TMS$_4$, LiTFSM (10% wt) | $4 \times 10^{-5}$ | $4.5 \times 10^{-4}$ |

Example 11

Electrochemical stability of a MG-20-TMS$_4$-based electrolyte is determined.

The MG-20-TMS$_4$-based electrolyte solution described in Example 10 was used in the following electrochemical cell configuration:

Li/MG-20-TMS$_4$, LiTFSM (10% wt)/Al.

The cell was tested by cyclic voltammetry between 0 and 5 Volt v. lithium at 10 mV/sec at 100° C. to establish the extent of the electrochemical stability window of the electrolyte. As illustrated in FIG. 1, the electrochemical stability window is in excess of 4.5 V, even at elevated temperature.

Example 12

Ionic conductivity of solid polymer electrolyte is determined.

A solid polymer electrolyte precursor solution was prepared using 75% wt of MG-20-TMS$_4$ (as in example 2) functioning as a plasticizer, 10% wt of MG-20-TMS$_2$ACR$_2$ (as in example 7) functioning as a polymerizable monomer, 5% wt of polyethylene glycol di-acrylate (PEGDA), and 10% wt of TFSI. A small amount of photoinitiator Darocure ® 1173 was added. The solution was coated on an aluminum foil and exposed to a source of UV radiation. A solid polymer membrane is obtained. The ionic conductivity of this membrane is $5.5 \times 10^{-5}$ S/cm at 25° C. and $4.3 \times 10^{-4}$ S/cm at 100° C.

Example 13

Ionic conductivity of a gel-polymer electrolyte is determined.

A gel-polymer electrolyte precursor solution was prepared using 55% wt of MG-20-TMS$_4$ (as in example 2) functioning as a plasticizer, 10% wt of MG-20-TMS$_2$ACR$_2$ (as in example 7) functioning as a polymerizable monomer, 5% wt of PEGDA, 20% wt of ethylene carbonate (EC), and 10% wt of LiTFSI. A small amount of photoinitiator Darocure ® 1173 was added. The solution was coated on an aluminum foil and exposed to a source of UV radiation. A solid polymer membrane is obtained. The ionic conductivity of this membrane is $3.3 \times 10^{-4}$ S/cm at 25° C. and $2.5 \times 10^{-3}$ S/cm at 100° C.

Example 14

Composite electrode is prepared.

A composite electrode, to be used in a lithium rechargeable battery, was prepared using 18 g of LiCoO$_2$, 4 g of carbon black, and 18 g of a solid polymer electrolyte precursor comprising of 4 g MG-20-TMS$_4$ (as in example 2), 9 g MG-20-TMS$_2$ACR$_2$ (as in example 5), 4 g of TMPEOTA (trimethyl propane ethoxylate triacrylate), 1 g of PEO, and a small amount of t-butyl peroctoate (Lucidol). The composite cathode formulation was coated on aluminum foil and cured thermally at 80° C. for approximately 2 h. Thermal processing is possible because no volatile plasticizer is present. The solid polymer electrolyte composite cathode formed a self supporting membrane having good electrical conductivity and electrochemical performance.

Example 15

LiAl anode cycling of a electrochemical cell is performed.

An electrolyte as described in example 10 was used to make the following electrochemical cell:

Li/MG-20-TMS$_4$, LiTFSM (10% wt)/Al-LiAl.

The cell was maintained at 95° C. and cycled at 50 micro-amperes/cm$^2$. The Li cycling efficiency of the LiAl electrode was greater than 99% after 50 cycles.

Example 16

MG-20-salt ionic conductivity is determined. Electrolyte solutions are prepared by dissolving LiTFSI or MG-20-Na in N-methyl pyrrolidone in various concentrations. Ionic conductivity are reported in the following table. The macro-ion MG-20-Na exhibits comparable conductivity to that of TFSI, while having the additional advantage of reduced anionic mobility in solution because of the large size of the anion.

TABLE 3

Comparative ionic conductivities of ionic salt solutions.

| Temperature (°C.) | LiTFSI-NMP (S/cm) | | MG-20-Na-NMP (S/cm) | |
|---|---|---|---|---|
| | 1% wt | 5% wt | 1% wt | 5% wt |
| 25 | $1.6 \times 10^{-3}$ | $8 \times 10^{-3}$ | $4.4 \times 10^{-4}$ | $8.9 \times 10^{-4}$ |
| 65 | $2 \times 10^{-3}$ | $1 \times 10^{-2}$ | $7.2 \times 10^{-4}$ | $1.5 \times 10^{-3}$ |
| 100 | $3.2 \times 10^{-3}$ | $1.6 \times 10^{-2}$ | $9.4 \times 10^{-4}$ | $2 \times 10^{-3}$ |

What is claimed is:

1. A solid polymer electrolyte, comprising:
   a cation selected from the group consisting of alkali metal and alkaline earth elements; and
   a polymer constituted from a functionalized alkoxylated carbohydrate, said carbohydrate selected from the group consisting of monosaccharides and oligosaccharides of pentoses and hexoses and having one to five hydroxyl groups per monosaccharide unit;
   wherein a total of between 4 and 150 alkoxy groups per monosaccharide unit are attached through ether linkages to said hydroxyl groups,
   wherein each terminal alkoxyl group of each alkoxide-substituted hydroxyl group of said carbohydrate is functionalized with a functional group, Y, selected from the group consisting of polymerizable functionalities, plasticizing agents and ionic species, and wherein at least one of said functional group, Y, of an alkoxide-substituted hydroxyl group comprises a plasticizing agent and wherein at least one said functional group, Y, of an alkoxide-substituted hydroxyl group comprises a polymerizable functionality, such that said polymer is obtained from polymerization at the polymerizable functionality.

2. A solid polymer electrolyte, comprising:

a cation selected from the group consisting of alkali metal and alkaline earth elements; and a polymer constituted from a functionalized alkoxylated carbohydrate, said carbohydrate selected from the group consisting of monosaccharides and oligosaccharides of pentoses and hexoses and having one to five hydroxyl groups per monosaccharide unit;

wherein a total of between 4 and 150 alkoxyl groups per monosaccharide unit are attached through ether linkages to said hydroxyl groups, wherein each terminal alkoxyl group of each alkoxide-substituted hydroxyl group of said carbohydrate is functionalized with a functional group, Y, selected from the group consisting of polymerizable functionalities plasticizing agents and ionic species, and wherein said alkoxide-substituted hydroxyl .groups are functionalized such that at least one Y of a first alkoxide-substituted hydroxyl group comprises a polymerizable functionality, at least one Y of a second alkoxide-substituted hydroxyl group comprises a plasticizing agent and at least one Y of a third alkoxide-substituted hydroxyl group comprises an ionizing species, such that said polymer is obtained from polymerization at the polymerizable functionality.

3. The electrolyte of claim 1, further comprising:

a plasticizer, said plasticizer comprising:

a carbohydrate selected from the group consisting of monosaccharides and oligosaccharides of pentoses and hexoses and having up to five hydroxyl groups per monosaccharide unit;

wherein a total of between 4 and 150 alkoxyl groups per monosaccharide unit are attached through ether linkages to said hydroxyl groups, such that each said hydroxyl group has at least one attached alkoxyl group; and wherein each terminal alkoxyl group of each alkoxide-substituted hydroxyl group of said carbohydrate is functionalized with a functional group, Y, selected from the group consisting of polymerizable functionalities, plasticizing agents and ionic species, further characterized in that at least one terminal alkoxyl group is functionalized with a plasticizing functionality.

4. The electrolyte of claim 1, further comprising:

a macro-ion, said macro-ion comprising:

a carbohydrate selected from the group consisting of monosaccharides and oligosaccharides of pentoses and hexoses and having up to five hydroxyl groups per monosaccharide unit;

wherein a total of between 4 150 alkoxyl groups per monosaccharide unit are attached through ether linkages to said hydroxyl groups, such that each said hydroxyl group has at least one attached alkoxyl group; and wherein each terminal alkoxyl group of each alkoxide-substituted hydroxyl group of said carbohydrate is functionalized with a functional group, Y, selected from the group consisting of polymerizable functionalities, plasticizing agents and ionic species, further characterized in that at least one terminal alkoxyl group is functionalized with an ionic species.

5. The electrolyte of claim 1, wherein at least one Y of a alkoxide-substituted hydroxyl group comprises an ionic species, whereby said carbohydrate functions as a macro-ion.

6. The electrolyte of claim 3, further comprising:

a macro-ion, said macro-ion comprising:

a carbohydrate selected from the group consisting of monosaccharides and oligosaccharides of pentoses and hexoses and having up to five hydroxyl groups per monosaccharide unit;

wherein a total of between 4 and 150 alkoxyl groups per monosaccharide unit are attached through ether linkages to said hydroxyl groups, such that each said hydroxyl group has at least one attached alkoxyl group; and wherein each terminal alkoxyl group of each alkoxide-substituted hydroxyl group of said carbohydrate is functionalized with a functional group, Y, selected from the group consisting of polymerizable functionalities, plasticizing agents and ionic species, further characterized in that at least one terminal alkoxyl group is functionalized with an ionic species.

7. The electrolyte of claim 1, 2, 3, 4, 5 or 6, wherein said electrolyte comprises an alkali metal salt selected from the group consisting of $LiCF_3SO_3$, $LiClO_4$, $LiSCN$, $LiBF_4$, $LiAsF_6$, $CF_3SO_3Li$, $LiPF_6$, $LiN(CF_3SO_2)_2$, $Li\ C(CF_3SO_2)_3$, $CF_3CO_2Li$ and mixtures thereof, said alkali metal salt being the source of said cation.

8. The electrolyte of claim 1, wherein said ionic species is the source of said cation, said ionic species comprising an anionic component bound to a terminal alkoxyl group and said cation.

9. An electrochemical device, comprising:

the electrolyte of claim 1, 2, 3, 4, 5, 6, a negative electrode; and a positive electrode separated from said negative electrode and also in contact with said electrolyte.

10. The electrochemical device of claim 39, wherein said electrolyte further comprises a plasticizer.

11. A polymer constituted from a functionalized alkoxylated carbohydrate, said carbohydrate selected from the group consisting of monosaccharides and oligosaccharides of pentoses and hexoses and having one to five hydroxyl groups per monosaccharide unit;

wherein a total of between 4 and 150 alkoxyl groups per monosaccharide unit are attached through ether linkages to said hydroxyl groups; and wherein each terminal alkoxyl group of each alkoxide-substituted hydroxyl group of said carbohydrate is functionalized with a functional group, Y, selected from the group consisting of polymerizable functionalities, plasticizing agents and ionic species, wherein at least one of said functional group, Y, of an alkoxide-substituted hydroxyl group comprises a plasticizing agent and wherein at least one said functional group, Y, of an alkoxide-substituted hydroxyl group comprises a polymerizable functionality, such that said polymer is obtained from polymerization at the polymerizable functionality.

12. The polymer of claim 11 wherein said polymerizable functionality is selected from the group consisting of epoxides, alkenyls, isocyanates, halosilyls, acrylates, methacrylates, cinnamates, fumarates and maleates.

13. The polymer of claim 11, wherein said plasticizing agent is selected from the group consisting of trialkylsilyls, alkyls, alkylnitriles, phosphate esters, phosphinate esters and saturated esters.

14. The polymer of claim 11, wherein said ionic species is selected from the group consisting of alkaline metal alkoxides, alkali metal salts of carboxylic acid and alkali metal salts of sulfonic acids.

* * * * *

UNITED STATES PATENT AND TRADEMARK OFFICE
CERTIFICATE OF CORRECTION

PATENT NO. : 5,433,876
DATED : July 18, 1995
INVENTOR(S) : Fauteux et al.

It is certified that error appears in the above-indentified patent and that said Letters Patent is hereby corrected as shown below:

Col. 1, line 8     After Additives". insert -- The invention was made with Government support contract number 93-F151600-000 awarded by the Central Intelligence Agency --.

Signed and Sealed this

Twelfth Day of August, 1997

Attest:

BRUCE LEHMAN

*Attesting Officer*     *Commissioner of Patents and Trademarks*